United States Patent [19]

Palosi et al.

[11] 4,304,938

[45] Dec. 8, 1981

[54] PROCESS FOR THE PREPARATION OF 3-PHENOXYBENZENES

[75] Inventors: Endre Palosi; Gergely Heja; Dezso Korbonits; Pál Kiss; Csaba Gönczi; Judit Cser née Kun; Ida Szvoboda née Kauzel; Gábor Kovács; Gabor Szabo; Tamás Kállay; Lászlo Ledniczky, all of Budapest, Hungary

[73] Assignee: Chinoin Gyógyszer és Vegyeszeti Termékek Gyára RT, Budapest, Hungary

[21] Appl. No.: 106,102

[22] Filed: Dec. 21, 1979

[30] Foreign Application Priority Data

Dec. 22, 1978 [HU] Hungary .............................. CI 1886

[51] Int. Cl.$^3$ ........................................... C07C 131/00
[52] U.S. Cl. ............................. 564/265; 260/340.9 R
[58] Field of Search ................. 260/340.9 R; 564/265, 564/266

[56] References Cited

U.S. PATENT DOCUMENTS 3,821,253  6/1974  Fried et al. .................. 260/340.9 R

*Primary Examiner*—Dolph H. Torrence
*Attorney, Agent, or Firm*—Karl F. Ross

[57] ABSTRACT

3-Phenoxybenzene derivatives are prepared by a method which comprises the steps of (a) chlorinating benzaldehyde with chlorine gas in the presence of a hydrocarbon and a Lewis acid catalyst to obtain 3-chlorobenzaldehyde; (b) reacting the 3-chlorobenzaldehyde with ethylene glycol to obtain 2-(3-chlorophenyl)-1,3-dioxolane; (c) etherifying said dioxolane with an alkali phenolate to yield the intermediate 2-(3-phenoxyphenyl)-1,3-dioxolane and converting this intermediate to the corresponding aldehyde, cyanohydrin, sulfonic acid salt or oxime derivative.

4 Claims, No Drawings

PROCESS FOR THE PREPARATION OF 3-PHENOXYBENZENES

The present invention relates to a new process for the preparation of 3-phenoxybenzenes of the formula

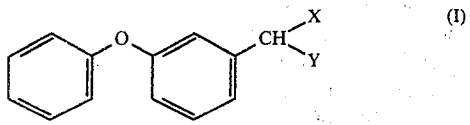

wherein
X is hydroxyl,
Y is hydrogen, SO$_3$Na or cyano, or
X and Y together represent an oxygen or an =NOH group It is well known that compounds of the formula I are useful intermediates in the production of various pharmaceutically active compounds and plant protecting agents, and can be prepared by methods known in the art (see for example U.S. Pat. No. 4,065,505; Published German Patent Applications Nos. 2 741 764, 2 744 603, 2 704 512, 2 651 371, 2 402 457 and 2 707 232; and Belgian Pat. No. 809 867).

According to the known methods starting from m-cresol or 3-phenoxybenzaldehyde 3-phenyoxybenzaldehyde serving as a key intermediate is prepared by a multi-step synthesis. Since the m-cresol used as a starting material should be of high purity, the known methods are expensive.

According to a further method 3-phenoxybenzaldehyde can be prepared by heating 3-bromo-benzaldehyde or an acetale thereof with sodium or potassium phenolate in an aprotic organic solvent, in the presence of pyridine and copper or a cuprous salt, at a temperature of 50° to 200° C. (Published German Patent Application No. 2 624 360). A drawback of this method is that it involves a bromination step (Org. Synth. Coll. Vol. V. 120, and Belgian Pat. No. 842 178).

Although theoretically 3-chlorobenzaldehyde appears to be the most promising starting compound, it is practically not used in the known methods, since both chlorination of benzaldehyde and etherification of 3-chlorobenzaldehyde can be carried out only with very low yields. The yield for the above-mentioned chlorination reaction is 43% (Org. Synth. Coll. Vol. V. 120), while etherification can be effected with a yield of 5 to 10% (Published German Patent Application No. 2 624 360 and Belgian Patent 842 177). The total yield of the synthesis route calculated for benzaldehyde amounts to 3%; the process is therefore extremely uneconomical.

3-Phenoxybenzyl alcohols of the formula II

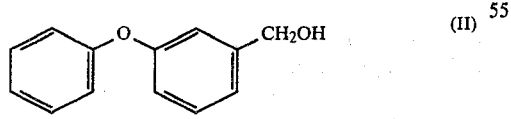

and III

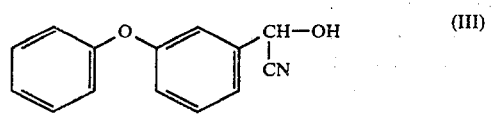

respectively have hitherto been prepared essentially following the methods described hereinbefore (Published German Patent Application Nos. 2 604 474, 2 604 473, 2 741 864, 2 744 603, 2 704 512, 2 651 371, 2 402 457 and 2 707 232).

According to a further known method 3-phenoxybenzaldehyde is reacted with formaldehyde corresponding to a mixed Cannizzaro reaction (Published Japanese Patent Specification No. 73 78135). This process, however, can be accomplished with an acceptable yield only in a very limited temperature range.

The present invention provides a new method for the preparation of compounds of the formula I—wherein X and Y are as defined hereinbefore—by one of the steps (A), (B) and (C). In step (A) benzaldehyde is chlorinated with chlorine gas, in the presence of a hydrocarbon and a Lewis acid catalyst, 3-chlorobenzaldehyde obtained is reacted with ethylene glycol, dioxolane derivative of the formula VIII

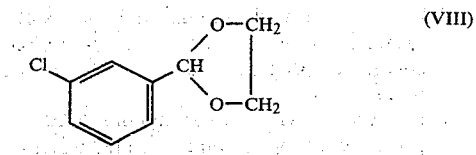

obtained is reacted with an alkali salt of phenol, and the dioxolane derivative of the formula VII

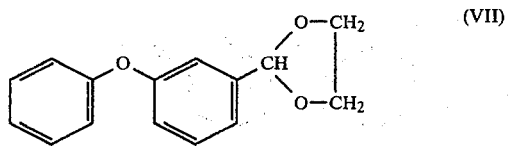

(a) is hydrolyzed, to prepare an aldehyde of the formula VI

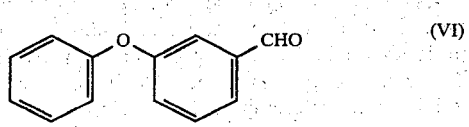

and if desired, is reduced with an aluminum or magnesium alkoxide having 2 to 4 carbon atoms, or (b) is reacted with an alkali cyanide in the presence of water and a water-immiscible organic solvent, and with a phase transfer into catalyst, to prepare a a cyanohydrin derivative of the formula III, or

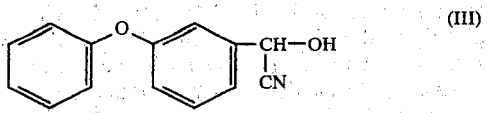

(c) is reacted with sodium hydrogensulfite in the presence of water and a water-miscible organic solvent, to prepare a sulfonic acid salt of the formula IV, or

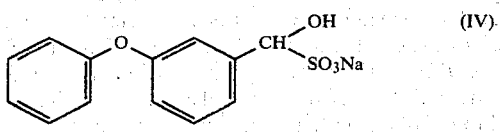

(d) is reacted with a hydroxylammonium salt in the presence of water and a water-miscible organic solvent, to prepare an oxime of the formula V; or

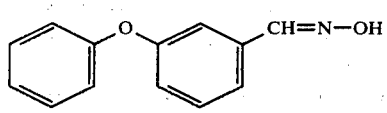

In step (B) a dioxolane derivative of the formula VII
(a) is hydrolyzed, to prepare an aldehyde of the formula VI, which is, if desired, reduced with an aluminum or magnesium alkoxide having 2 to 4 carbon atoms to prepare an alcohol of the formula II, or
(b) is reacted with an alkali cyanide in the presence of water and a water-immiscible organic solvent and a phase transforming catalyst, to prepare a cyanohydrin derivative of the formula III, or
(c) is reacted with sodium hydrogensulfite in the presence of water and a water-miscible organic solvent to prepare a sulfonic acid salt of the formula IV, or
(d) is reacted with a hydroxylammonium salt in the presence of water and a water-miscible organic solvent to prepare an oxime of the formula V.
(c) an aldehyde of the formula VI is reduced with an aluminum or magnesium alkoxide having 2 to 4 carbon atoms, to prepare an alcohol of the formula II

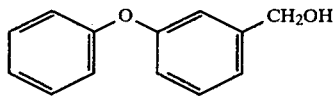

Chlorination of benzaldehyde is performed with chlorine gas, using a chlorinated hydrocarbon as a solvent, in the presence of a Lewis acid catalyst.

As the Lewis acid ferric chloride or preferably aluminum chloride can be used, in an amount of 1 to 3 moles, preferably 2 to 2.1 moles pro 1 mole of benzaldehyde. The molar proportion of benzaldehyde to chloride gas is 1:1–1:1.1, preferably 1:1.02 to 1:1.04.

The reaction is accomplished in a halogenated hydrocarbon such as chloroform, dichloromethane.tetrachloroethane, especially 1,2-dichloroethane, 2 to 4 moles/lit.,—preferably 2 to 3 moles/lit.—solutions of benzaldehyde are used.

Chlorination is effected between 20° and 50° C., preferably 25° and 35° C.

If desired, 3-chlorobenzaldehyde can be separated by vacuum distillation, but it is preferred to boil the organic solution of 3-chlorobenzaldehyde with ethylene glycol, in the presence of an acidic catalyst without separation, until no more water is condensed.

As an acidic catalyst strong mineral acids, e.g. hydrochloric acid, sulfuric acid; aromatic sulfonic acids, i.e. benzenesulfonic acid, p-toluene-sulfonic acid; or strongly acidic ion-exchanging resins, i.e. Amberlite IR-120, Dowex 50 W, Varion KS, can be used.

According to a preferred embodiment of the claimed process a solution of 3-chlorobenzaldehyde in 1,2-dechloroethane which has been obtained as a result of chlorination step, is boiled with 1 to 1.3 moles of ethylene glycol calculated for 1 mole of benzaldehyde, and with 3 to 5 g. of the ion-exchanging resin Varion KS. 2-(3-chlorophenyl)-1,3-dioxolane obtained if desired, can be separated by distillation in vacuo, or more advantageously, can be melted together with an alkali phenolate in the presence of an metal catalyst, immediately after evaprating off the solvent.

As an alkali phenolate preferably potassium phenolate is used, expediently in a slight (0.1 to 0.4 moles) excess. To obtain a more dilute melt, the reaction is carried out in phenol. 2 to 2.5 moles of phenol are used per mole of 2-(3-chlorophenyl)-1,3-dioxolane.

As a catalyst copper powder and/or cuprous chloride can be used in an amount of 5 to 15% by moles.

The reaction temperature can be varied between 190° and 250° C., preferably 195° and 205° C.

2-(3-phenoxyphenyl)-1,3-dioxolane prepared in this way if desired, can easily be converted into the corresponding free 3-phenoxybenzaldehyde by treating with an aqueous mineral acid or with a strongly acidic ion-exchanging resin in an aqueous medium. 3-Phenoxybenzaldehyde is reduced with metal alkoxides. As a metal component alkaline earth metals, i.e. calcium, magnesium; and aluminum can be used. As an alcohol component lower alcohols, e.g. methanol, ethanol, propanol, isopropanol, butanol, isobutanol, sec.-butanol, ter.-butanol are employed.

According to a preferred embodiment of our process 3-phenoxybenzaldehyde is reduced with an aluminum alkoxide. More particularly, a solution of 3-phenoxybenzaldehyde in an organic solvent is heated with aluminum alkoxide. As an organic solvent lower alcohols, preferably those corresponding to the alkoxy moiety of the aluminum alkoxide employed; aromatic hydrocarbons, preferably benzene or toluene can be used. Especially preferred aluminum alkoxides are aluminum ethoxide and aluminum isopropoxide. 0.1 to 1 moles, preferably 0.15 to 0.7 moles of aluminum alkoxide are used per mole of 3-phenoxybenzaldehyde. The temperature of the reaction mixture is kept at 20° to 120° C., preferably at the boiling point of the solvent used. With respect to the progress of the reaction it is advantageous to eliminate continuously the oxo-compound corresponding to the alkoxy moiety of the aluminium alkoxide, which is formed as a by-product, from the reaction mixture.

In a further preferred embodiment of the process according to the invention 3-phenoxybenzaldehyde is reduced with sodium dihydro-bis-(2-methoxyethoxy)-aluminate in an organic solvent, preferably in toluene.

2-(3-Phenoxyphenyl)-1,3-dioxolane, which is the key compound of our invention, is an excellent starting material for the preparation of various 3-phenoxybenzaldehyde derivatives.

The sulfonic acid salt of the formula IV is for example prepared by treating the dioxolane derivative of the formula VII with a saturated aqueous sodium hydrosulfite solution at 0° to 100° C., with stirring. To assist the reaction a water-miscible oranic solvent, preferably an aliphatic alcohol, more preferably methanol is added to the reaction mixture. The reaction is accelerated by phase transforming catalysts, preferably quaternary ammonium compounds or crown ethers. As a quaternary ammonium compound for example tetrabutylammonium chloride, tetrabutylammonium bromide, triethylbenzylammonium chloride, tricaprylylmethylammonium chloride, cetyltrimethylammonium chloride or trimethylbenzylammonium chloride can be used. Preferred crown ethers are for example 18-crown-6, dicyclohexal-18-crown-6 and dibenzo-18-crown-6.

3-Phenoxybenzaldehyde oxime of the formula V can also easily be prepared starting from the dioxolane derivative of the formula VII. To prepare this compound dioxolane derivative of the formula VII is heated with an excess amount of hydroxylammonium chloride or hydroxylamine sulfate in a mixture of water and an organic solvent, at a temperature of 20° to 100° C. As organic solvents aliphatic alcohols having 1 to 4 carbon atoms, such as methyl, ethyl, propyl alcohol can be employed.

Also 3-phenoxybenzaldehyde cyanohydrin of the formula III can advantageously be prepared following the method of the invention. For this purpose a dioxolane compound of the formula VII is treated with a dilute mineral acid, preferably hydrochloric acid or sulfuric acid, in the presence of a water-immiscible organic solvent, preferably an aromatic hydrocarbon (benzene, toluene, xylene), at a temperature of 50° to 150° C. The reaction mixture is reacted with an aqueous solution of an alkali cyanide, preferably in the presence of a phase-transforming catalyst. As an alkali cyanide sodium or potassium cyanide can be employed, and as phase-transforming catalysts the same compounds are employed which have been listed in connection with the preparation of bisulfite derivatives.

Cyanohydrin compound of the formula III can further be prepared through the bisulfite compound of the formula IV obtained directly from dioxolane compound of the formula VII, by means of an alkali cyanide, in the presence of a water-miscible dipolar aprotic organic solvent, e.g. dimethyl formamide, dimethyl sulfoxide or acetonitrile.

Further detailed of our invention are illustrated in the following Examples but it is not intended to limit the scope of the invention to the Examples.

EXAMPLE 1

A mixture of 198 g. of m-phenoxy-benzaldehyde and 1 liter of a 1 M solution of aluminum isopropoxide in isopropyl alcohol is distilled through a distillation column until acetone can be detected in the distillate by means of 2,4-dinitrophenyl-hydrazine. Distillation takes about 2 to 3 hours. The excess of isopropyl alcohol is distilled off in vacuo. To the residue 500 g. of ice and 550 ml. of a 20% aqueous hydrochloric acid solution are added. The separated oil is shaken with two 1-liter portions of benzene, the benzene solution is dried over sodium sulfate. After distilling off benzene, 195 g. (97.4%) of m-phenoxybenzyl alcohol are obtained. According to gas chromatography the purity of the product is higher than 95%.

EXAMPLE 2

To a solution of 198 g. of m-phenoxy-benzaldehyde in 1 liter of absolute ethanol 60 g. of aluminum ethoxide are added. The reaction mixture is allowed to stand at room temperature. The reaction mixture is then evaporated under atmospheric pressure. From the residue following the procedure of Example 1 198 g. (98.9%) of m-phenoxybenzyl alcohol are prepared in a purity over 95% (according to gas chromatography).

EXAMPLE 3

From 16.33 g. aluminum chips, 250 ml. of isopropyl alcohol, 11 ml. of carbontetrachloride and 0.1 g. of mercuric chloride, aluminum isopropylate is prepared. To the isopropylate obtained 350 ml. of isopropyl alcohol and 198.2 g. of 3-phenoxy-benzaldehyde are added, and the reaction mixture is kept at 45° to 50° C. for 2.5 hours, and subsequently at 80° C. for 0.5 hours, whereupon it is further manufactured as described in Example 1.

197 g. (98%) of 3-phenoxybenzyl alcohol are obtained, boiling at 138° C./0.1 mmHg.

EXAMPLE 4

From a mixture of 16.33 g. of aluminum chips, 100 ml. of toluene and 0.1 g. of mercuric chloride and a solution of 11 ml. of carbontetrachloride and 140 ml. of isopropyl alcohol a solution of aluminum isopropylate in toluene is prepared. A solution of 198.2 g. of 3-phenoxybenzaldehyde in 70 ml. of toluene is added, and the reaction mixture is kept at 45° to 50° C. for 3 hours.

The solvent is distilled off and the residue is manufactured as described in Example 3 to yield 197 g. (98%) of 3-phenoxybenzyl alcohol.

EXAMPLE 5

To a solution of 96 g. of 3-phenoxybenzaldehyde in 100 ml. of toluene 85 ml. of a 70% solution of sodium dihydro-bis-(2-methoxyethoxy)-aluminate in toluene is added at a temperature below 40° C. dropwise, under cooling. The pH of the cooled reaction mixture is then adjusted to 1 with a 20% aqueous hydrochloric acid solution. The two phases are separated. Upon distilling of toluene a crude product is obtained with a near quantitative yield, which can directly be used for further reactions. Distillation in vacuo yields 85 g. (85%) of 3-phenoxybenzyl alcohol having a boiling point of 129° to 132° C./0.05 mmHg.

$n_D^{27} = 1.5900$.

EXAMPLE 6

To a suspension of 205 g. of anhydrous aluminum chloride in 300 ml. of 1,2-dichloroethane 81 g. of benzaldehyde are poured at 35° C. It is stirred for 30 minutes, whereupon 56.2 g. of chlorine gas is introduced into the mixture at 27° to 29° C. The reaction mixture is stirred at 30° to 33° C. for an additional two hours and is subsequently poured on a mixture of 1 kg. of ice and 60 ml. of concentrated hydrochloric acid. The aqueous phase is extracted with 1,2-dichloroethane. The combined dichloroethane solutions are washed with water, 48 g. of ethyleneglycol and 3 g. of a strongly acidic ion-exchanging resin (Various KS) are added, and the mixture is boiled until condensation of water terminates. Dichloroethane is distilled off and the residue is subjected to vacuum fractionation. 99 g (70%) of 3-(3-chlorophenyl)-1,3-dioxolane are obtained, boiling at 108° to 110° C./3 mmHg. The purity of the product is better than 95% (determined by gas chromatography); $n_D^{25} = 1.5369$.

Analysis for $C_9H_9ClO_2$: Calculated: Cl=19.2%, Found: Cl=19.01%.

EXAMPLE 7

To 301 g. of phenol 109 g. of potassium hydroxide are added, and water is distilled off from the reaction mixture by raising the temperature to 200° C. The melt obtained is cooled to 180° C., 5 g. of copper powder and 10 g. of cuprous chloride are added, whereupon 277 g. of 2-(3-chlorophenyl)-1,3-dioxolane are slowly poured into the reaction mixture with stirring, keeping the reaction temperature between 195° and 205° C. The mixture is then stirred at 200° to 205° C. for 3.5 hours. 500 ml. of xylene are added to the reaction mixture at 130° C., the ptrcipitated salt is filtered off and washed with 200 ml. of xylene. The filtrate is washed to neutral with aqueous sodium hydroxide and sodium chloride solutions. Evaporation of the residue in vacuo yields 265 g. (73%) of 2-(3-phenoxyphenyl)-1,3-dioxolane, melting at 143° to 146° C./0.1 mmHg;

$n_D^{26} = 1.5736$.

EXAMPLE 8

As a starting material a solution of crude 2-(3-phenoxyphenyl)-1,3-dioxolane obtained in Example 7 after neutralization is used. The solution in xylene is boiled with a mixture of 48 ml. of concentrated sulfuric acid and 530 ml. of water with stirring for 3 hours. Upon cooling the phases are separated. 211 g. (71%) of 3-phenoxybenzaldehyde are obtained, boiling at 128° to 130° C./0.4 mmHg. The yield is calculated for the starting material of Example 7. The purity of the obtained product is better than 95% (determined by gas chromatography);

$n_D^{20} = 1.5955$.

EXAMPLE 9

Following the procedure of Example 7 but using 150 g. of phenol 54.6 g. of potassium hydroxide, 2.5 g. of copper powder and 5 g. of cuprous chloride, crude 2-(3-chlorophenyl)-1,3-dioxolane (138 g.) according to Example 6 is converted into 2-(3-phenoxyphenyl)-1,3-dioxolane without further purification. 93 g. of 2-(3-phenoxyphenyl)-1,3-dioxolane are obtained, boiling at 143° to 146° C./0.1 mmHg;

$n_D^{26} = 1.5737$.

Yield: 50% calculated for benzaldehyde. The purity of the product obtained is better than 95% (determined by gas chromatography).

EXAMPLE 10

To a solution of 24.2 g. of 2-(3-phenoxyphenyl)-1,3-dioxolane in 120 ml. of methanol a solution of 41.6 g. of sodium hydrogensulfite in 120 ml. of water is added, and the reaction mixture is boiled until no traces of starting compound can be detected by thin layer chromatography. The reaction mixture is cooled, the precipitated crystals are filtered off, washed with a 50% aqueous methanol solution and dried at 60° to 80° C. 27 g. (89.5%) of 3-phenoxybenzaldehyde bisulfite are obtained.

EXAMPLE 11

To a solution of 24.2 g. of 2-(3-phenoxyphenyl)-1,3-dioxolane in 150 ml. of ethyl alcohol a solution of 14 g. of hydroxylammonium chloride in 150 ml. of water is added, and the mixture is boiled until no traces of starting compound can be detected by thin layer chromatography (silica gel, 1:1 mixture of benzene and tetrachloromethane, development: by UV light). Alcohol is distilled off and the aqueous residue is cooled in ice water. The precipitated crystals are filtered off. 20 g. (94%) of 3-phenoxybenzaldehyde oxime are obtained, melting at 45° to 46° C.

EXAMPLE 12

A solution of 2-(3-phenoxyphenyl)-1,3-dioxolane prepared according to Example 7 in xylene is treated with an aqueous sulfuric acid solution as described in Example 8. The reaction mixture is cooled and 83 g. of tetrabutylammonium chloride are added followed by a dropwise addition of a solution of 100 g. of sodium cyanide in 500 ml. of water at 10° to 20° C. Thereafter a solution of 48 ml. of concentrated sulfuric acid in 500 ml. of water is added dropwise and the reaction mixture is stirred until no traces of starting compound can be detected by thin layer chromatography. From the xylene phase 196 g. of 3-phenoxybenzaldehyde cyanehydrin are isolated. The purity of the product obtained is better than 95% (determined by NMR spectroscopy). Yield: 58% calculated for 2-(3-chlorophenyl)-1,3-dioxolane.

EXAMPLE 13

Into 150 ml. of dimethyl formamide 60.45 g. of 3-phenoxybenzaldehyde bisulfite are added, whereupon a solution of 12.51 g. of sodium cyanide in 60 ml. of water is poured into the mixture at 5° to 10° C. under cooling with ice water, in 25 to 35 minutes. The mixture is stirred to 10° to 12° C. for 1 hour and 62 ml. of acetic acid are added at 10° to 15° C., dropwise, in 25 to 30 minutes. The reaction mixture is stirred for an additional 20 minutes, whereupon it is poured into a vigurously stirred mixture of 500 ml. of water and 300 ml. of ethylacetate. From the organic phase 44 g. of 3-phenoxybenzaldehyde cyanehydrin are isolated. The purity of the product obtained is better than 95% (determined by NMR spectroscopy).

What we claim is:

1. A process for the preparation of a compound of the formula (V)

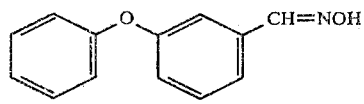

which comprises the steps of:
(a) chlorinating benzaldehyde with chlorine gas in the presence of a chlorinated hydrocarbon and a Lewis acid catalyst to obtain 3-chloro-benzaldehyde;
(b) reacting the 3-chlorobenzaldehyde with ethylene glycol to yield a compound of the formula VIII:

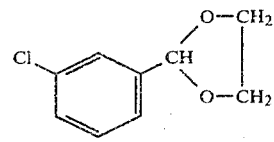

(c) etherifying the compound of formula VIII with an excess of alkali phenolate in the presence of Cu powder and Cu(I)Cl in phenol at a temperature of 105° C. to 205° C. to yield a compound of the formula VII:

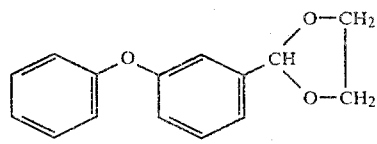

and:
(d) forming the desired product by reacting the compound of formula VII with a hydroxylammonium salt in the presence of water and a water-miscible organic solvent.

2. The process defined in claim 1, step (d), wherein the hydroxylammonium salt is hydroxylammonium chloride or hydroxylammonium sulfate and the water-miscible organic solvent is an aliphatic alcohol having 1 to 4 carbon atoms.

3. A process for the preparation of a compound of the formula (V)

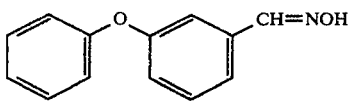

which comprises the step of:

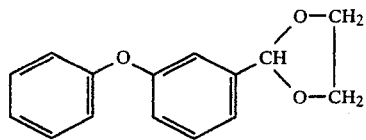

with a hydroxylammonium salt in the presence of water and a water-miscible organic solvent.

4. The process defined in claim 3 wherein the hydroxylammonium salt is hydroxylammonium chloride or hydroxylammonium sulfate and the water-miscible organic solvent is an aliphatic alcohol having 1 to 4 carbon atoms.

* * * * *